United States Patent

Swoyer et al.

[11] Patent Number: 5,800,496
[45] Date of Patent: Sep. 1, 1998

[54] MEDICAL ELECTRICAL LEAD HAVING A CRUSH RESISTANT LEAD BODY

[75] Inventors: John M. Swoyer, Andover; Peter B. McIntyre, Mounds View; James E. Upton, New Brighton; Annette M. Hebzynski, Spring Lake Park; Joseph F. Lessar, Coon Rapids, all of Minn.

[73] Assignee: Medtronic, Inc., Minneapolis, Minn.

[21] Appl. No.: 672,011

[22] Filed: Jun. 24, 1996

[51] Int. Cl.$^6$ ........................................ A61N 1/05
[52] U.S. Cl. .................. 607/122; 607/119; 600/374; 600/377
[58] Field of Search ..................... 128/642; 607/119, 607/122, 123, 126–128; 600/373–375, 377, 381

[56] References Cited

U.S. PATENT DOCUMENTS

| | | |
|---|---|---|
| 3,664,347 | 5/1972 | Harmjanz . |
| 4,284,896 | 8/1981 | Grigorov et al. . |
| 4,514,589 | 4/1985 | Aldinger et al. . |
| 4,651,751 | 3/1987 | Swendson et al. ............ 607/122 |
| 4,759,378 | 7/1988 | Swendson et al. . |
| 4,945,342 | 7/1990 | Steinemann . |
| 5,014,721 | 5/1991 | Hirschberg . |
| 5,246,438 | 9/1993 | Langberg .................... 128/642 |
| 5,330,521 | 7/1994 | Cohen ........................ 607/122 |
| 5,466,253 | 11/1995 | Doan . |
| 5,575,814 | 11/1996 | Giele et al. ................. 607/127 |
| 5,584,873 | 12/1996 | Shoberg et al. ............. 607/122 |

OTHER PUBLICATIONS

"Anatomical and Morphological Evaluation of Pacemaker Lead Compression" by Donald M. Jacobs et al; Pacing and Clinical Electrophysiology, vol. 16, No. 3, Mar. 1993 Part I.

*Primary Examiner*—Lee S. Cohen
*Assistant Examiner*—David M. Ruddy
*Attorney, Agent, or Firm*—Michael J. Jaro; Harold Patton

[57] ABSTRACT

A medical lead which has a connector assembly coupled to an electrode by a lead body, the lead body is designed so as to have greater resistance to crush fatigue in the area which is located between the rib and clavicle when implanted. In particular the lead body of the present invention features an insulative sheath covering a coiled conductor. The coiled conductor has three sections, viz., proximal, intermediate and distal sections. The intermediate section has a different pitch as compared to proximal section and distal section. In the preferred embodiment, intermediate section has a pitch of approximately 0.100 while proximal section has a pitch of approximately 0.025 and distal section has a pitch of approximately 0.025. Moreover, intermediate section has a length of approximately 10.4 inches while proximal section has a length of approximately 5.1 inches and distal section has a length of approximately 7.2 inches. In such a manner the lead of the present invention presents a coiled conductor having a greater pitch in the area in which crush fatigue between the clavicle and rib is likely to occur.

26 Claims, 3 Drawing Sheets

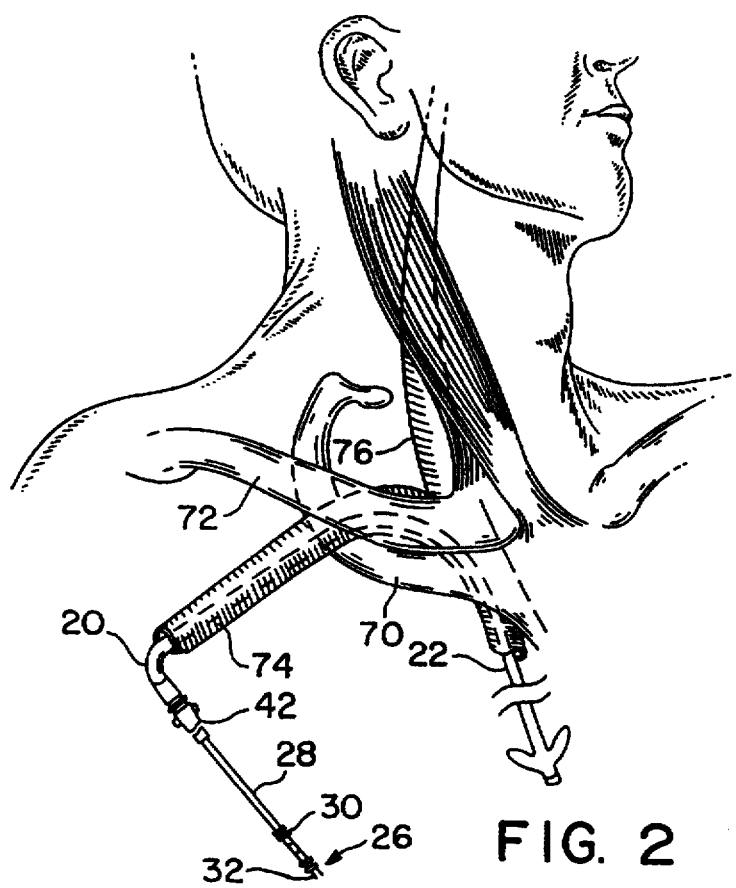
FIG. 2
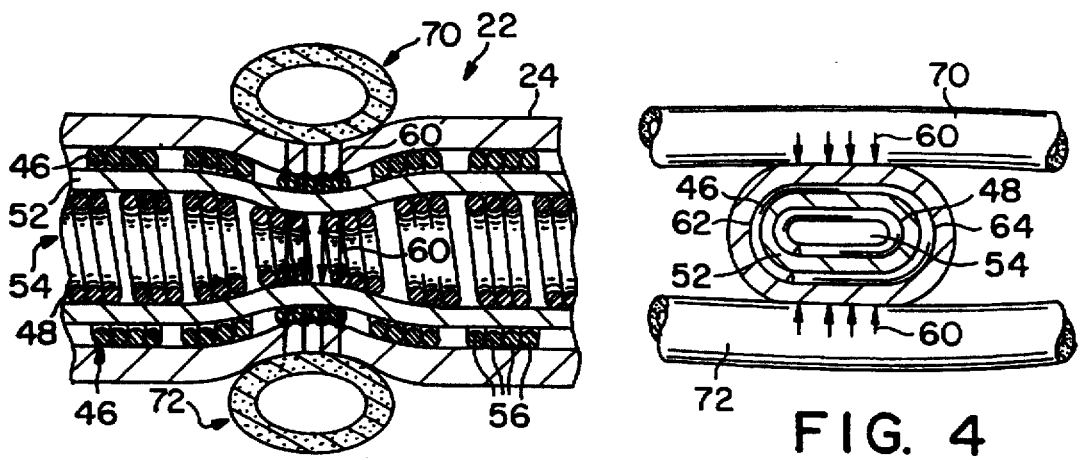
FIG. 3
(PRIOR ART)
FIG. 4

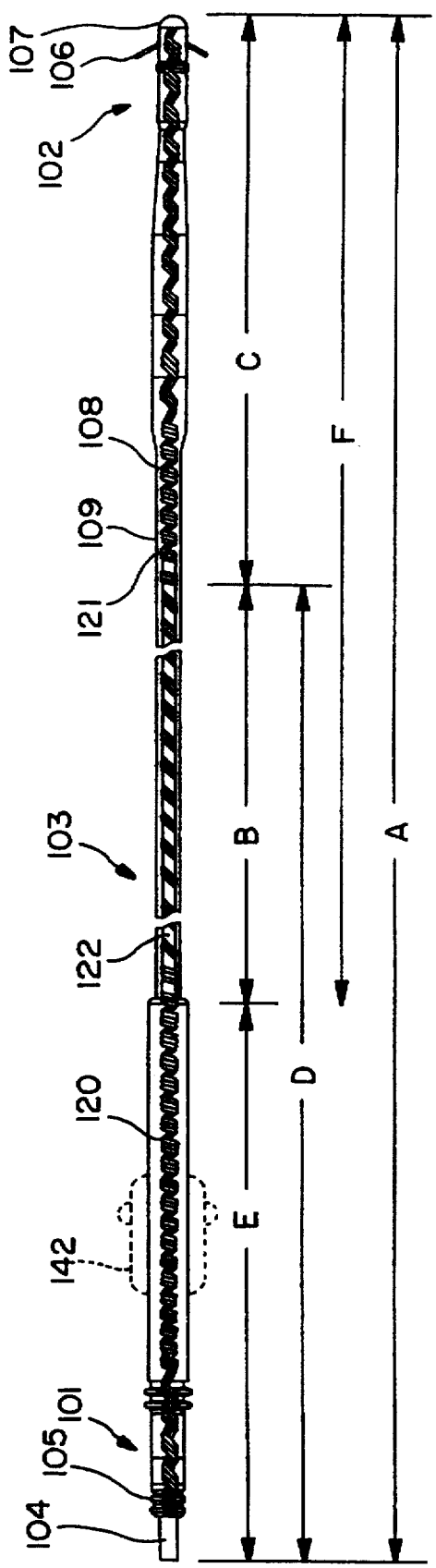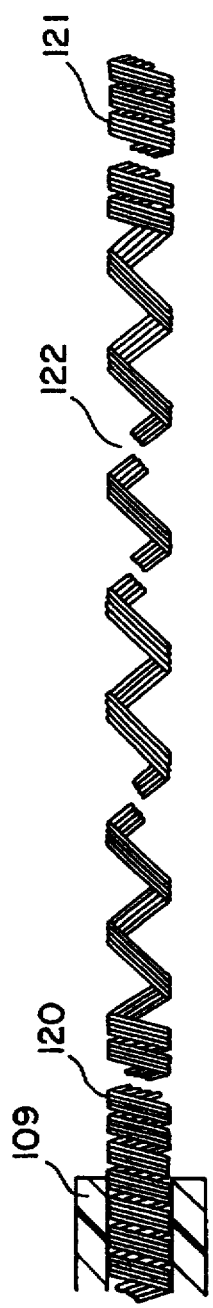
FIG. 5
FIG. 6

MEDICAL ELECTRICAL LEAD HAVING A CRUSH RESISTANT LEAD BODY

FIELD OF THE INVENTION

This invention relates to the field of body implantable medical electrical leads, and in particular to a body implantable medical electrical lead which features a crush resistant lead body.

BACKGROUND OF THE INVENTION

In the medical field, various types of body implantable leads are known and used. One type of commonly used implantable lead is an endocardial pacing lead.

Endocardial pacing leads are attached at their proximal end to an implantable pulse generator and at their distal end to the endocardium of a cardiac chamber. The distal end of an endocardial lead may engage the endocardium by either an active fixation mechanism or a passive fixation mechanism.

Active fixation mechanisms use a structure, such as helix or hook, to physically engage into or actively affix themselves onto the heart. Passive fixation mechanisms, such as a tine assembly, lodge or passively fix themselves to the heart.

A preferred means for introducing an endocardial lead into the heart is through a vein. Specifically, such a lead, called a transvenous lead, is introduced into and maneuvered through the vein so the distal end is positioned within the heart. Generally, both active fixation as well as passive fixation leads are introduced into the heart in this manner.

Various designs of transvenous leads have been disclosed. U.S. Pat. No. 4,287,896 of Grigorov et al. discloses an electrode for connecting to an internal organ. The electrode is designed for transvenous implantation and features a coiled conductor to provide longitudinal stability to the electrode while it is conducted along a transvenous route during implantation. In particular the conductor has varying pitch with the coils at each end portion spaced more closely together as compared to the mid portion. Each end portion, furthermore, has a length of no more than double the distance from the place the electrode contacts the organ to the point it exits the organ. In particular the length of each end portion, as a rule, could not exceed 100 to 150 mm or 3.93 to 5.91 inches.

A multi-step procedure is often used to introduce such leads within the venous system. Generally this procedure consists of inserting a hollow needle into a blood vessel, such as the subclavian vein. A wire guide is then passed through the needle into the interior portion of the vessel. The needle is then withdrawn and an introducer sheath and dilator assembly is then inserted over the wire guide into the vessel. The assembly is advanced into a suitable position within the vessel, i.e. so that the distal end is well within the vessel but the proximal end is outside the patient. Next the dilator and wire guide are removed. The introducer sheath is left in position and therefore offers direct access from outside the patient to the interior of the blood vessel. In such a fashion a lead can be passed into the vessel through the introducer sheath and ultimately be positioned within the heart. Finally the introducer sheath is removed from the body.

One difficulty which has been encountered with endocardial leads implanted in this manner is crush. In particular leads implanted in this manner are located between the clavicle and a rib. Over time, the clavicle and the rib may impinge upon the lead and compress it. This may lead, eventually, to the coiled conductor of the lead to be crushed and eventually fracture. This may affect lead performance and ultimately affect the performance of the implantable pulse generator.

SUMMARY OF THE INVENTION

It is accordingly an object of the present invention to provide a medical electrical lead which has a crush resistant lead body.

This object is accomplished by providing a medical lead which has a connector assembly coupled to an electrode by a lead body, the lead body is designed so as to have greater resistance to crush fatigue in the area which is located between the rib and clavicle when implanted. In particular the lead body of the present invention features an insulative sheath covering a coiled conductor. The coiled conductor has three sections, viz., proximal, intermediate and distal sections. The intermediate section has a different pitch as compared to proximal section and distal section. In the preferred embodiment, intermediate section has a pitch of approximately 0.100 while proximal section has a pitch of approximately 0.025 and distal section has a pitch of approximately 0.025. Moreover intermediate section has a length of approximately 10.4 inches while proximal section has a length of approximately 5.1 inches and distal section has a length of approximately 7.2 inches. In such a manner the lead of the present invention presents a coiled conductor having a greater pitch in the area in which crush fatigue between the clavicle and rib is likely to occur.

DETAILED DESCRIPTION OF THE DRAWINGS

FIG. 1 illustrates the positioning of a pacing system implanted within a patient.

FIG. 2 illustrates the right side neck shoulder area of a patient.

FIG. 3 is a detailed side sectional view of a prior art medical electrical lead undergoing crush between the clavicle and a rib.

FIG. 4 is an axial sectional view of the prior art medical electrical lead shown in FIG. 3 which is undergoing crush between the clavicle and a rib.

FIG. 5 shows a side view of the medical electrical lead according to the present invention.

FIG. 6 is a detailed view showing the intermediate portion of the conductor coil used in the medical electrical lead of the present invention;

It should be noted the drawings are not necessarily to scale.

BRIEF DESCRIPTION OF THE DRAWINGS

FIG. 2 illustrates the right side neck shoulder area of a patient. In FIG. 2, the first rib 70 and right clavicle 72 of the skeletal structure are illustrated. The subclavian vein 74 passes between the first rib 70 and right clavicle 72 before merging with the internal jugular vein 76 and proceeding to the heart (not shown). The pacing lead 20 is inserted into the subclavian vein 74, and extends through the rib 70 clavicle 72 crossing point and down the jugular vein to the heart (not shown). A fixation sleeve 42, which may be either fixed or slidably mounted around lead body 22, serves to stabilize the pacing lead 20 at the site of venous insertion.

Figure 1:
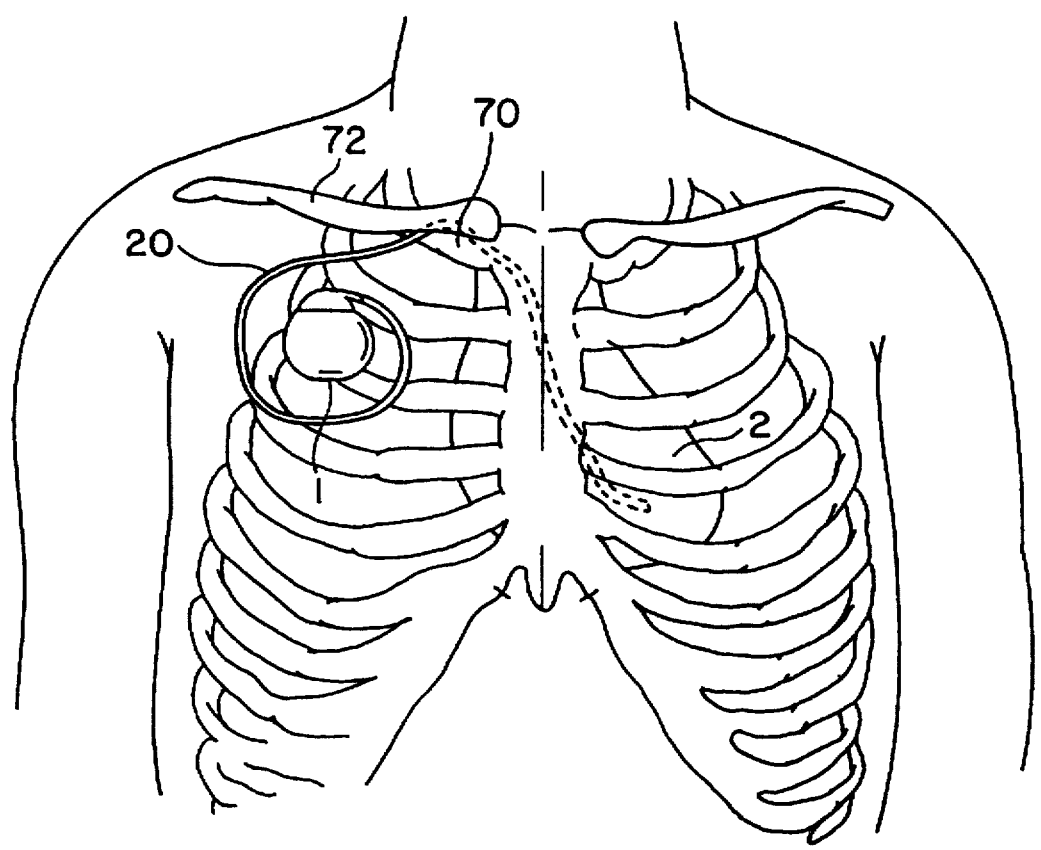
FIG. 1 illustrates the positioning of a pacing system implanted within a patient. As seen, implantable pulse generator 1 is electrically coupled to heart to by medical electrical lead 20. As discussed above, a popular manner to achieve venous access for a transvenous lead is in the sub clavian region.

An enlarged cross sectional view of a portion of a pacing lead of the prior art in the area of the rib 70 clavicle 72 crossing point is illustrated in the axial view of FIG. 3 and the cross sectional view of FIG. 4. The lead body illustration includes two conductors 46, 48, separated by insulation tubing 52, all contained within the insulation sheath 24. The spiral winding of the conductor(s) 46, 48 results in a hollow central area 54, and allows the lead body 22 to re main quite flexible. Also, the hollow central area 54 accommodates insertion of a guide wire or stylet (not shown) which is relatively stiff and which allows the doctor to guide and control the implantation of the pacing lead 20.

The axial view in FIG. 3 of the lead body 22, in the area traversing between the first rib 70 and clavicle 72, illustrates the problem addressed by the present invention. In FIG. 3, the outer conductor 46 is illustrated as being contained between the insulation sheath 24 on the out side and an insulation tubing 52 at its inner diameter. The conductor 46, as discussed above, is a helically wound conductor, and therefore the axial view depicts cross sections of the conductor 46. In addition, it should be understood that the conductor 46 may be made up of a plurality of conductors contained in a bundle 56 to provide redundancy while also retaining flexibility by reducing the cross sectional thickness which would be required for a single conductor. In addition, the second conductor 48 which is also helically wound is disposed internally of the insulation tubing 52.

The hollow central area must be maintained in order to allow insertion of the stylet to guide implantation. Accordingly, the lead body illustrated in FIGS. 3 and 4 is subject to crushing by the first rib 70 and clavicle 72 during various activities performed by the recipient of the pacing system. The structural forces exerted on the conductor 46, as well as the insulation tubing 52, are identified by the arrows 60. It must also be recognized that the cylindrical structure of the lead body 22 will require that the constriction caused by the first rib 70 and clavicle 72 illustrated in FIG. 2 will cause flattening of the lead body 22, which results in sharp bending deformation of the coil conductors 46 and 48, as illustrated in the cross sectional view of FIG. 4 at locations 62 and 64.

FIG. 5 depicts a plan sectional view of the lead according to the present invention. As seen, lead 100 features connector assembly 101 coupled to electrode assembly 102 by lead body 103. Connector assembly 101 features connector pin 104 and sealing rings 105 to permit the lead to be coupled into an implantable pulse generator, as is well known in the art.

Electrode assembly 102 features tines 106 and electrode 107. Electrode 107 is preferably constructed of a porous, sintered platinum electroplated with platinum black, as is well known in the art. Electrode 107 may further feature a monolithic controlled release device (MCRD) is positioned nearby. Such a MCRD is preferably loaded with an anti-inflammatory agent, e.g., a steroid dexamethasone sodium phosphate. The steroid is also deposited with the pores of the electrode 107 as is also well known in the art. Other agents may also be used, such as beclomethasone phosphate.

Electrode 107 is coupled to connector assembly 101 through lead body 103. As seen, lead body 103 features conductor 108 insulated with insulative sleeve 109. Insulative sleeve 109 is preferably a smooth silicone sheath as is well known in the art. Fitted about lead body 103 is fixation sleeve 142, as is well know in the art.

Conductor 108 is a multifilar coiled conductor which has essentially three sections: proximal section 120, distal section 121, coupled together by intermediate section 122. As seen, distal section 121 and proximal section 120 feature a coiled conductor which is wound having a lower pitch as compared to intermediate section 122.

Turning now to FIG. 6 which shows a detailed view of the conductor 108. As seen, conductor 108 is a multifilar coiled conductor preferably conducted out of a platinum alloy such as MP35N. As seen, intermediate section 122 has a different pitch as compared to proximal section 120 and distal section 121. In the preferred embodiment, intermediate section 122 has a pitch of 0.100 while proximal section 120 has a pitch of 0.025 and distal section has a pitch of 0.025. Of course, various other pitches may be used. Moreover, although in the preferred embodiment, distal section 121 and proximal section 120 have equivalent pitches, each of these sections may feature different pitches from all the other sections.

Turning again to FIG. 5, as seen, lead 100 has a length A. In the preferred embodiment, A is 22.8 inches. Intermediate section 122 of conductor 108 has a length B. In the preferred embodiment, B is equal to 10.4 inches. Intermediate section 122 is positioned such that its distal end is located a distance C from the distal end of lead 100. In the preferred embodiment, C is 7.2 inches. Similarly, the proximal end of intermediate section 122 is located a distant E from the proximal end of lead 100. In the preferred embodiment, E is equal to 5.1 inches. As also seen, proximal end of section 122 is located a distance F from the distal end of lead 100. In the preferred embodiment, distance F is equal to 17.6 inches. Similarly, distal end of section 122 is located a distance D from the proximal end of lead 100. In the preferred embodiment, distance D is equal to 15.5 inches.

As discussed above, these dimensions are critical to the intended functioning of the present invention. In particular, the distances C and D are carefully chosen such that the intermediate section 122 is, in 99.7% of all patients, located in the area of the lead subject to subclavian crush between the clavicle and the rib, as discussed above. Of course, all the dimensions as well as pitches discussed above, are in the preferred embodiment and may be substantially varied depending upon the patient, type of lead, and the location of the electrode of the lead within the patient. In particular, each of the above pitches and dimensions may be within the following ranges. Length A of lead 100 may be between approximately 16.8 to approximately 28.8 with 22.8 inches preferred. Length B of intermediate section 122 may be between approximately 4.4 to 16.4 with 10.4 inches preferred. Length C may be between approximately 4.2 to 10.2 with 7.2 inches preferred. Length D may be between approximately 10.5 to 20.5 with 15.5 inches preferred. Length E may be between approximately 3.1 to 7.1 with 5.1 inches preferred. Likewise proximal section 120 may have a pitch of between approximately 0.005 to 0.050 with a pitch of 0.025 preferred. Intermediate section 122 may have a pitch of between approximately 1.0 to 0.051 with a pitch of 0.100 preferred. Distal section may have a pitch of between approximately 0.005 to 0.050 with a pitch of 0.025 preferred.

It is to be understood, that the present invention is not limited to use only in atrial or ventricular pacing leads, but may be employed in many of various types of therapeutic or diagnostic devices including transvenous leads intended to be disposed at various places within patient 10, including, for example, leads intended to be disposed within the patient's coronary sinus, as well as various other types of electrical leads, including nerve, muscle or defibrillation leads. It is to be further understood, moreover, the present invention may be employed in introducing many of various types of therapeutic or diagnostic catheters and is not limited only to medical electrical leads. For purposes of illustration only, however, the present invention is below described in the context of a transvenous endocardial pacing lead. Moreover, although a specific embodiment of transvenous endocardial pacing lead has been disclosed, this is done for purposes of illustration only and is not intended to be limiting with regard to the scope of the invention. It is to be contemplated that various substitutions, alterations, and/or modifications may be made to the disclosed embodiment without departing from the spirit and scope of the invention as defined in the following claims.

What is claimed is:

1. A medical electrical lead comprising:

a connector assembly;

a coiled conductor having a distal end and a proximal end, the proximal end electrically coupled to the connector assembly, the coiled conductor having a proximal section, an intermediate section and a distal section, the distal section coiled with a first pitch, the intermediate section coiled with a second pitch, the second pitch greater than the first pitch, the distal section extending for a length of approximately 7.2 inches, the intermediate section extending for a length of approximately 10.5 inches, the proximal section having a third pitch, the third pitch less than the second pitch,;

an electrode electrically coupled to the distal section of the coiled conductor; and an insulative sheath covering the coiled conductor.

2. A medical electrical lead according to claim 1 further comprising the electrode is constructed of a porous sintered platinum.

3. A medical electrical lead according to claim 2 wherein the porous platinum electrode material is further electroplated with platinum black.

4. A medical electrical lead according to claim 1 wherein an exposed surface of the electrode is generally hemispherical in shape.

5. A lead according to claim 1 wherein the electrode is formed of porous metallic or other conductive materials from the class of materials consisting essentially of platinum, palladium, titanium, tantalum, rhodium, iridium, carbon, vitreous carbon and alloys, oxides and nitrides of such metals.

6. A medical electrical lead according to claim 1 wherein the insulative sheath covering the coiled conductor has a smooth cylindrical exterior.

7. A medical electrical lead which may be implanted in a typical human heart, comprising:

a connector;

an electrode for location in the right ventricular apex of the human heart when the lead is implanted in the human heart;

a conductor having a proximal end coupled to the connector and a distal end coupled to the electrode the conductor having a first proximal section having a first pitch and a second intermediate section having a second pitch coupled to the first proximal section and a third distal section having a third pitch coupled to the second intermediate section, the third distal section of a length such that when the electrode is located in the right ventricular apex of the human heart, the second section may be located within the subclavian vein between the clavicle and the first rib; and an insulator covering the conductor between the electrode and the connector, the insulator having a smooth cylindrical exterior wherein the first pitch is between approximately 0.005 to 0.050, wherein the second pitch is between approximately 1.0 to 0.051, wherein the third pitch is between approximately 0.005 to 0.050.

8. A medical electrical lead according to claim 7 wherein the first pitch is approximately 0.025.

9. A medical electrical lead according to claim 7 wherein the second pitch is approximately 0.100.

10. A medical electrical lead according to claim 7 wherein the third pitch is approximately 0.025.

11. A medical electrical lead according to claim 7 wherein the first proximal section is between approximately 3.1 to 7.1 inches.

12. A medical electrical lead according to claim 11 wherein the first proximal section is approximately 5.1 inches.

13. A medical electrical lead according to claim 7 wherein the distal section extends for a length between approximately 4.2 to 10.2 inches.

14. A medical electrical lead according to claim 13 wherein the distal section extends for a length approximately 7.2 inches.

15. A medical electrical lead according to claim 7 wherein the intermediate section extends for a length between approximately 4.4 to 16.4 inches.

16. A medical electrical lead according to claim 15 wherein the intermediate section extends for a length approximately 10.4 inches.

17. A medical electrical lead comprising:

a connector assembly;

a coiled conductor having a distal end and a proximal end, the proximal end electrically coupled to the connector assembly, the coiled conductor having a proximal section, an intermediate section and a distal section, the distal section coiled with a first pitch, the intermediate section coiled with a second pitch, the second pitch greater than the first pitch, the proximal section coiled with a third pitch, the third pitch less than the second pitch;

an electrode electrically coupled to the distal section of the coiled conductor; and a insulative sheath covering the coiled conductor, the insulative sheath having a smooth exterior.

18. A medical electrical lead according to claim 17 wherein the distal section extends for a length between approximately 4.2 to 10.2 inches.

19. A medical electrical lead according to claim 18 wherein the distal section extends for a length approximately 7.2 inches.

20. A medical electrical lead according to claim 17 wherein the intermediate section extends for a length between approximately 4.4 to 16.4 inches.

21. A medical electrical lead according to claim 20 wherein the intermediate section extends for a length approximately 10.4 inches.

22. A medical electrical lead according to claim 17 wherein the first pitch is between approximately 0.005 to 0.050.

23. A medical electrical lead according to claim 22 wherein the first pitch is approximately 0.025.

24. A medical electrical lead according to claim 17 wherein the second pitch is between approximately 1.0 to 0.051.

25. A medical electrical lead according to claim 24 wherein the second pitch is approximately 0.100.

26. A method of implanting a system for stimulating tissue featuring a transvenous medical electrical lead comprising the steps of:

Inserting an introducer sheath and dilator assembly from the exterior of a patient into a blood vessel of the patient such that a distal end of the introducer sheath within the blood vessel and a proximal end is outside the patient;

inserting a transvenous medical electrical lead through the introducer sheath and into the blood vessel, the transvenous medical electrical lead having a connector, a conductor coupled to the connector, the conductor having a first proximal section having a first pitch and a second intermediate section having a second pitch coupled to the first proximal section and a third distal section having a third pitch coupled to the second intermediate section, the second pitch greater than either the first pitch or the third pitch, an electrode coupled to the third distal section and an insulator covering the conductor between the electrode and the connector, the insulator having a smooth cylindrical exterior;

moving the transvenous medical electrical lead through the blood vessel and into a heart of the patient until the electrode is positioned with the heart and the second intermediate section is positioned within the blood vessel between the clavicle and the first rib;

removing the introducer; and coupling the connector to a pulse generator.

* * * * *